United States Patent [19]

Child

[11] 4,221,548
[45] Sep. 9, 1980

[54] DUAL ACTION SOLENOID PUMP

[76] Inventor: Frank W. Child, Eagle Bend, Minn. 56446

[21] Appl. No.: 890,583

[22] Filed: Mar. 20, 1978

[51] Int. Cl.² ............................................. F04B 17/04
[52] U.S. Cl. ........................................ 417/418; 3/1.7; 128/1 D; 417/571
[58] Field of Search .............. 417/418, 417, 416, 570, 417/571; 92/162; 251/129; 310/14, 15, 23, 30, 34; 3/1.7; 128/1 D

[56] References Cited
U.S. PATENT DOCUMENTS

| | | | |
|---|---|---|---|
| 345,657 | 7/1886 | Wylie | 417/571 X |
| 461,295 | 10/1891 | Van Depoele | 417/418 |
| 1,391,968 | 9/1921 | Nyman | 417/571 X |
| 1,652,374 | 12/1927 | Price | 92/162 R |
| 2,686,280 | 8/1954 | Strong et al. | 417/418 X |
| 3,134,938 | 5/1964 | Morgan | 417/418 X |
| 3,479,959 | 11/1969 | Christensen | 417/418 |
| 3,740,171 | 6/1973 | Farkos | 417/418 |
| 3,835,475 | 9/1974 | Child | 137/527.8 |

*Primary Examiner*—Carlton R. Croyle
*Assistant Examiner*—Edward Look
*Attorney, Agent, or Firm*—Burd, Bartz & Gutenkauf

[57] ABSTRACT

A pump for moving a fluid, as blood, having a body and end members forming a cylindrical chamber. A free floating piston located in the chamber is moved along the length of the chamber with a solenoid to pump blood into and out of opposite ends of the chamber. The end members containing inlet and outlet valves and sleeves are adapted to attach to veins or tubes to carry the blood to and from the pump. When electrical power is applied to the solenoid, a magnetic force operates to move the piston in the chamber, thereby pumping blood into and out of the chamber through the valves in the opposite end members.

55 Claims, 8 Drawing Figures

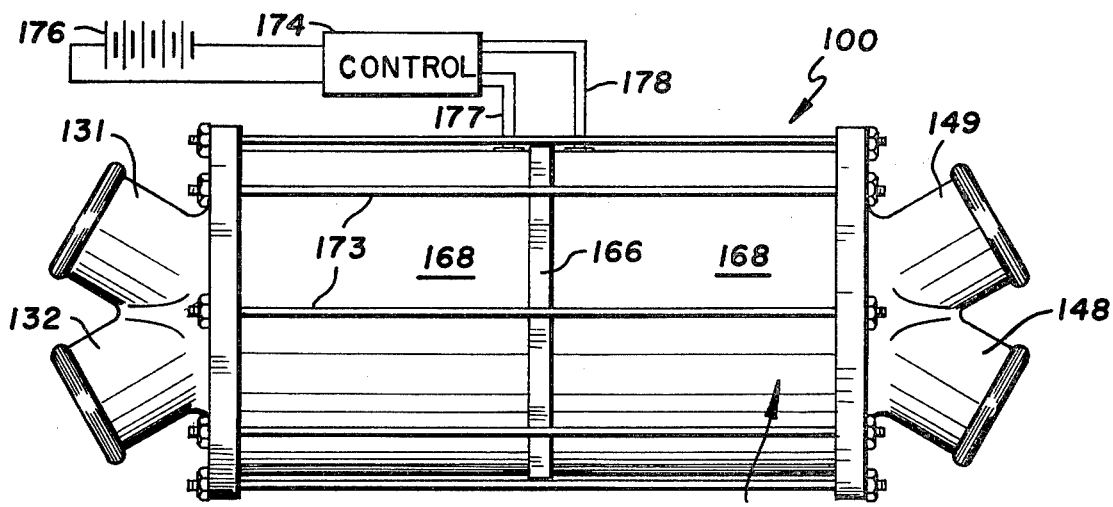
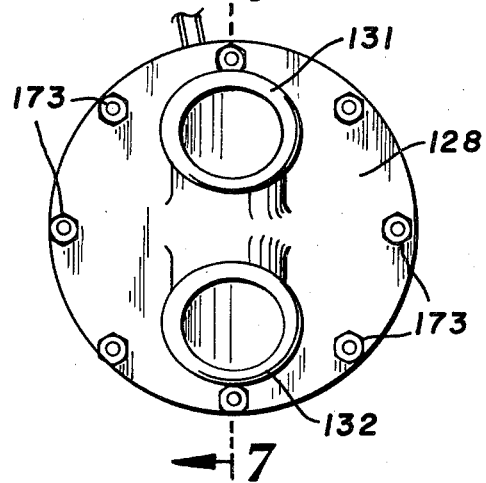
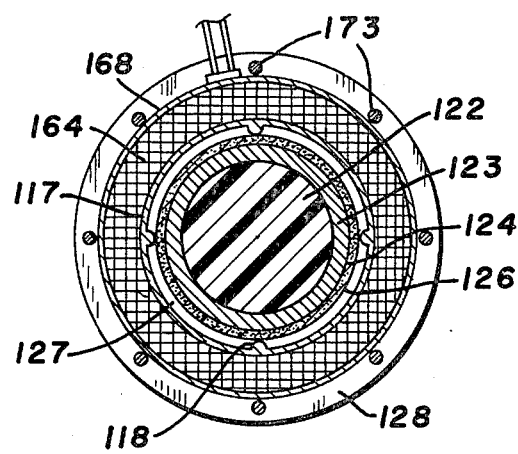
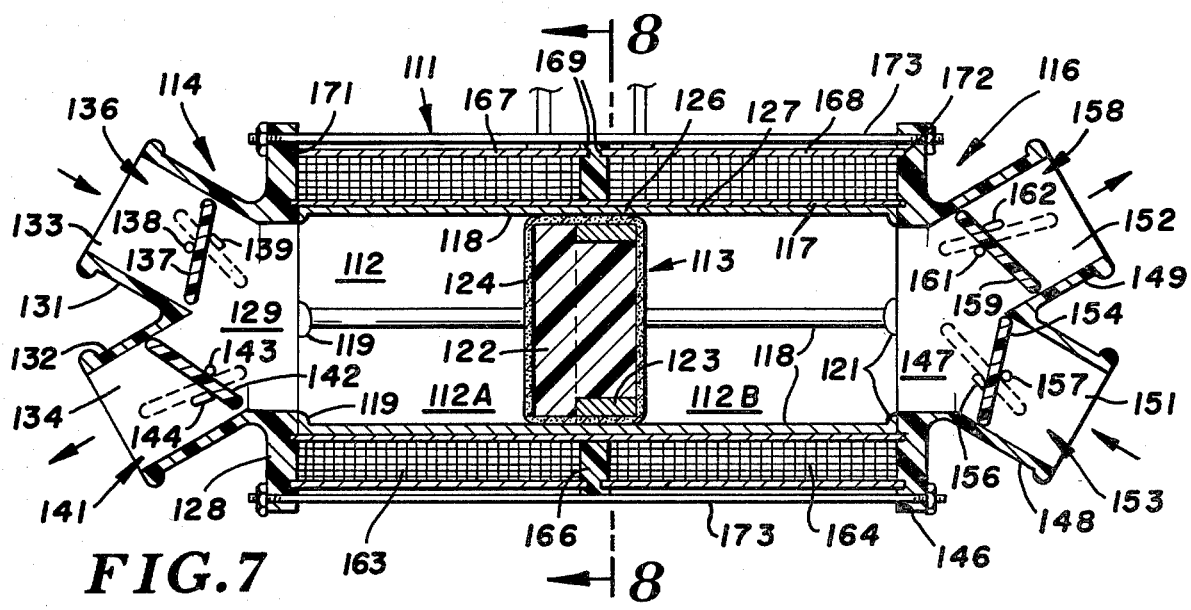
FIG. 5
FIG. 6
FIG. 8
FIG. 7

DUAL ACTION SOLENOID PUMP

SUMMARY OF INVENTION

The invention is directed to a pump for moving a fluid, as blood. The pump is a double-acting pumping apparatus that has a body having a cylindrical chamber. A piston moves in the chamber to move the fluid into and out of the opposite ends of the chamber. A solenoid surrounding the body is operable to drive the piston between the opposite ends of the chamber. End members mounted on opposite ends of the body have inlet and outlet passages for carrying the fluid into and out of the opposite ends of the chamber. Oneway valves located in the passages control the flow of fluid into and out of the opposite ends of the chamber. When electric power is applied to the solenoid, magnetic force functions reciprocate the piston in the chamber to effect pumping of the fluid.

The pump is operable to move blood in a manner that simulates the pumping action of a natural heart. The blood containing chamber is divided by the movable piston so that the pump simulates two chambers of the heart. The piston is enclosed within the blood chamber so that it does not allow any contamination of the blood, nor the leakage of the blood from the chamber. The controls for the solenoid are operable to automatically control the magnetic force applied to the piston and thereby control the pumping rate and pressure of the blood in the chamber.

IN THE DRAWINGS

FIG. 5 is a plan view of a modification of the pump of the invention;

FIG. 6 is an end elevational view of the left end of FIG. 5;

FIG. 7 is an enlarged sectional view taken along the line 7—7 of FIG. 6; and

FIG. 8 is a sectional view taken along the line 8—8 of FIG. 7.

DESCRIPTION OF PREFERRED EMBODIMENTS

Figure 1:
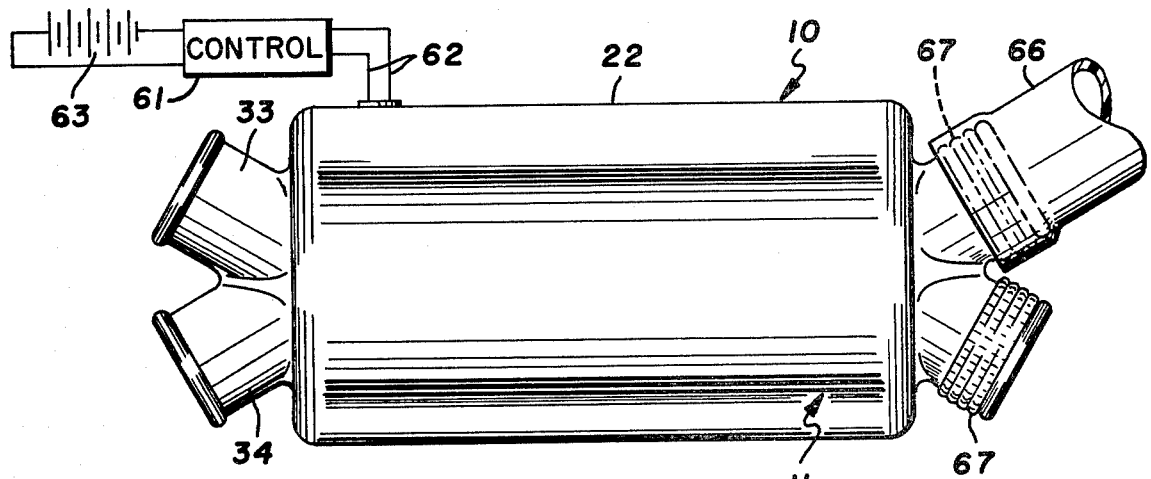
FIG. 1 is a plan view of the pump of the invention.
Figure 2:
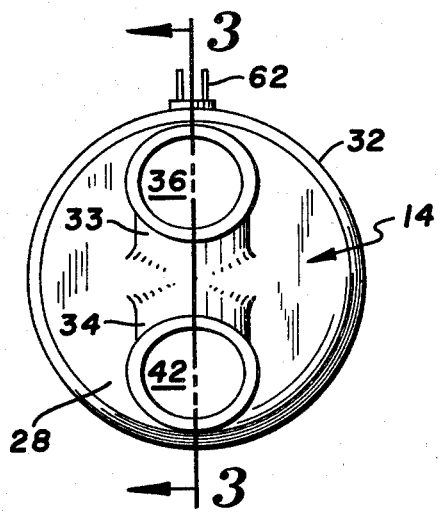
FIG. 2 is an end elevational view of the left end of FIG. 1.

Referring to the drawings, there is shown in FIG. 1 the fluid pump of the invention indicated generally at 10. Pump 10 is a dual or double-acting pump operable to move fluid in two pulses per cycle of movement of the pump piston. The pump is operable to move fluids, as water, oil, and biological fluids, such as blood. The pump hereinafter described will be described as a blood pump.

Pump 10 has a cylindrical body 11 surrounding a cylindrical chamber 12. A free floating valving member or disc piston 13 is located in chamber 12. Piston 13 is movable in response to electro-magnetic force to pump blood into and out of the opposite ends of chamber 12.

A first end assembly indicated generally at 14 is mounted on the left end of body 11. End assembly 14 has one-way inlet and outlet valves for controlling the flow of blood into and out of the left section 12A of chamber 12. The opposite end of body 11 carries the second end assembly indicated generally at 16. End assembly 16 also has one-way inlet and outlet valves for controlling the flow of blood into and out of the right section 12B of chamber 12. A solenoid having a coil or winding 21 located around wall 17 extends from flange 18 to end flange 19. The number of turns of the coil is selected to provide for the optimum flux densities and pumping pressures in the chamber 12. Walls 16 and 17 and casing 22 are made of materials that are biologically inert and compatible with the body tissues, including the blood. Wall 17 and casing 22 can be coated with a layer of pyrolite carbon as disclosed in U.S. Pat. No. 3,835,475.

Figure 4:
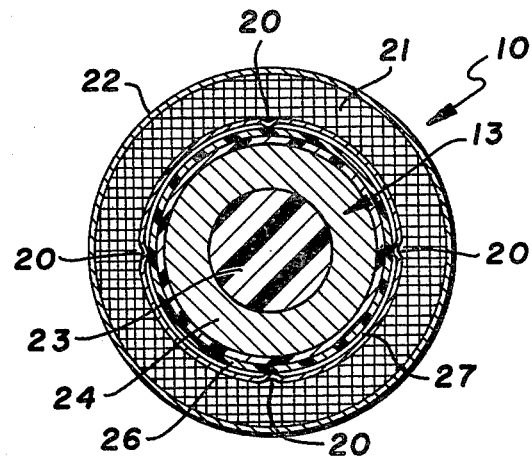
FIG. 4 is a sectional view taken along the line 4—4 of FIG. 3.
Figure 3:
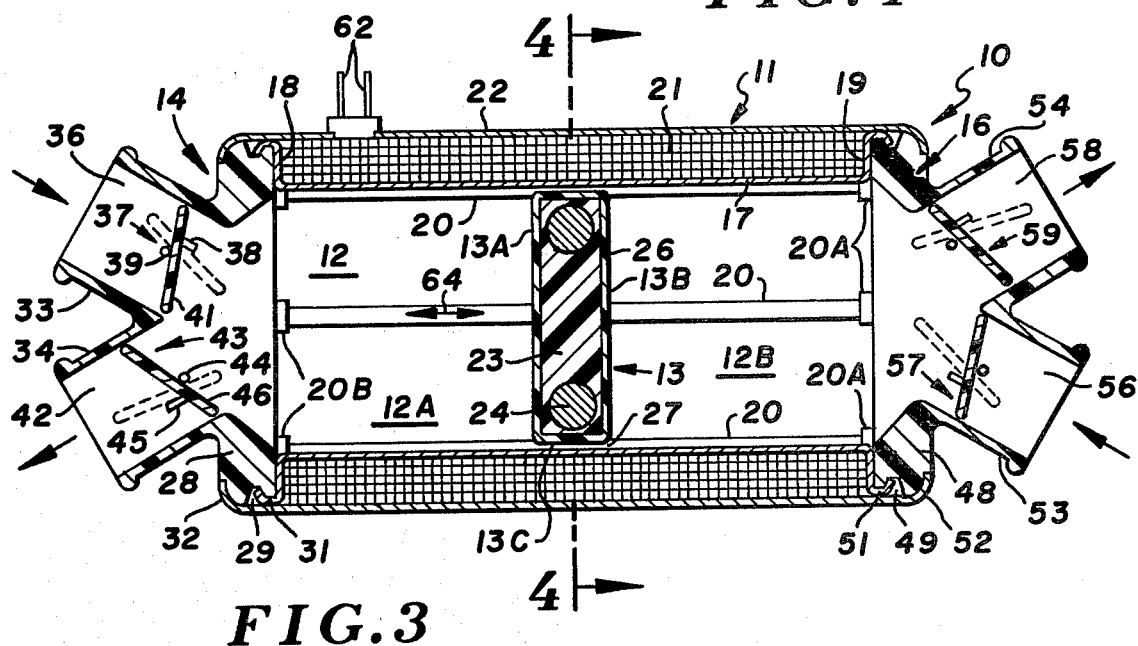
FIG. 3 is an enlarged sectional view taken along the line 3—3 of FIG. 2.

Piston 13, as shown in FIGS. 3 and 4, is a generally flat disc-like member having a circular substrate or core 23 of graphite, plastic or other lightweight material. A ring 24 of magnetic material, such as iron, or a cobalt iron alloy, is imbedded in the outer peripheral portion of core 23. Core 23 is covered with an outer skin or coating 26 of hard, wear-resistant and biologically inert material, such as pyrolite carbon. The material can be a silicon alloy pyrolite carbon as disclosed in U.S. Pat. Nos. 3,546,711 and 3,835,475.

As shown in FIG. 3, piston 13 has flat outside surfaces 13A and 13B extended generally transverse to the longitudinal axis of the chamber 12. The surfaces 13A and 13B join with a cylindrical outer peripheral surface 13C.

Wall 17 has a plurality of longitudinal lands or ribs 20. Ribs 20 are circumferentially spaced from each other and extend the entire length of wall 17. The opposite ends of ribs 20 are enlarged and form stop members 20A and 20B that are engaged by piston 13 to limit the opposite longitudinal movements of piston 13. Ribs 20 locate the outer cylindrical surface 13C of piston 13 a short distance inwardly from the wall 17. This provides separate arcuate spaces or passages 27 between chamber sections 12A and 12B. Passages 27 allow a sligth flow or leakage of blood past piston 15 to keep the blood moving in annular space 27 and chamber sections 12A and 12B, thereby avoiding clotting and damage to the blood tissue.

As shown in FIGS. 3 and 4, four separate arcuate passages 27 are spaced circumferentially around the piston 13. This insures that there is a slight flow of blood past the entire outer peripheral surface 13C of the piston. The piston 13 can rotate about its longitudinal axis as it reciprocates between stop members 20A and 20B.

End assembly 14 has a circular end member 28 attached to flange 18 and casing 22. The outer peripheral edge of member 28 has an outwardly open annular groove 29 receiving an inwardly turned lip 31 integral with the outer end of flange 18. Lip 31 holds the member 28 in fixed assembled relation with flange 18. Casing 22 has an inwardly turned end 32 that is curved down over the portion of end member 28.

A pair of outwardly directed tubular extensions or nipples 33 and 34 are adjoined to the center portion of end member 28. Nipple 33 has an inlet passage 36 leading to the chamber section 12A. A one-way valve unit 37 is located in passage 36. Valve unit 37 has pivot members 38 and 39. A pivoting disc or valving element 41 is operatively carried by pivot members 38 and 39. Disc 41 functions to permit the flow of blood into chamber 12A and restricts the flow of blood out of chamber 12A. Pivot members 38 and 39 and disc 41 can be constructed in accordance with the heart valve disclosed in U.S. Pat. No. 3,835,475. Other types of one-way valves, as ball valves and double leaflet valves, can be used to control the flow of blood through nipple passage 36.

Nipple 34 has an outlet passage 42 in communication with the chamber section 12A. A one-way valve unit 43 is located in passage 42 to control the flow of blood out through passage 42. Valve unit 43 has pivot members 44 and 45 carrying a pivoted disc or valving member 46. Disc 46 is operatively associated with pivot members 44 and 45 in a manner to permit the flow of blood out of the chamber section 12A through passage 42 and restrict reverse flow from passage 42 back into chamber section 12A. Valving unit 43 can be constructed in accordance with the heart valve disclosed in U.S. Pat. No. 3,835,475. Other types of one-way valves can be used with nipple 34 to control the outlet flow of blood from the chamber section 12A. Other examples of suitable one-way valves are shown in U.S. Pat. Nos. 3,130,419; 3,416,159; 3,476,143; 3,632,212; and 3,824,629.

End assembly 16 has a circular end member 48 provided with an outwardly open annular groove 49. An inwardly turned lip integral with the flange 19 is turned over into the groove 49 to secure the end member to flange 19. Casing 22 has an end that is turned down over the end member 28, thereby attaching the casing to the end member. Other types of structures can be used to connect the wall 17 and casing 22 to the end members 14 and 16, respectively.

End member 48 has a pair of tubular extensions or nipples 53 and 54 adapted to be connected to veins or tubing with suitable attaching structures, such as sutures. Nipple 53 has an inlet passage 56. A one-way inlet valve unit 57 is located in passage 56. Valve unit 57 is operable so as to allow blood to flow into the chamber section 12B and restrict the reverse or outflow of blood from the chamber section 12B. Nipple 54 has an outlet passage 58 in communication with the chamber section 12B. A one-way outlet valve unit 59 is located in the inlet end of passage 58. Valve unit 59 allows the flow of blood out of chamber section 12B and restricts the reverse or inflow of blood from passage 58 to chamber 12B. Valve units 57 and 59 follow the construction of the valve units 37 and 43.

A control circuit 61 is connected to the solenoid coil 21 with suitable leads 62. A power source 63 is coupled to control unit 61. The power source 63 can be rechargeable batteries or an outside power source. Control 61 is operable to reverse the flow of electric current through the solenoid coil 21 and thereby establishes sequential reverse flux fields or magnetic force which acts on iron ring 24 to move the piston 13 in opposite directions, as indicated by the arrow 64. Control 61 can be responsive to variations of both the inlet and outlet blood pressures to operate solenoid 21 in a manner which maintains the blood pressure with a normal natural range.

In use, the flux field established by solenoid coil 21 sequentially moves piston 13 from one end of chamber 12 to the opposite end of chamber 12. When piston 13 moves to the right, as shown in FIG. 3, the blood will flow through inlet passage 36 into the chamber section 12A. Valve unit 43 will be closed, thereby restricting the flow of blood from passage 42 into chamber 12A. Movement of the piston 13 to the right also causes the blood in the chamber section 12B to flow through the outlet valve 59 into the outlet passage 58. Valve unit 57 is closed, thereby restricting the flow of blood into passage 56. The blood is pumped out of chamber section 12B and is drawn into chamber section 12A. When the piston 13 reaches stops 20A the electric power to the solenoid coil 21 is reversed. This applies a reverse flux force on iron ring 24 moving the piston to the left into engagement with stops 20B. The blood in chamber section 12A will flow out through valve unit 43 and passage 42. Valve unit 37 is closed, thereby restricting the flow of blood through passage 36. Valve unit 57 will open allowing the blood to flow to passage 56 into chamber section 12B. Valve unit 59 closes to restrict the reverse flow of blood through passage 58 into chamber section 12B. The control 61 regulates the timing or sequence cycle of the piston 13 so that the blood is pumped according to the normal heart functions of a natural heart.

Referring to FIG. 5, there is shown a modification of the fluid pump, such as a blood pump, indicated generally at 100. Pump 100 has an elongated cylindrical body 111 surrounding a cylindrical pumping chamber 112. Pumping chamber 112 is divided into two separate chambers 112A and 112B with a reciprocating valving member or piston indicated generally at 113. Piston 113 is a cylindrical dis-like member that is slidably located in chamber 112 for reciprocating movement to opposite ends of chamber 112. End assemblies 114 and 116 are attached to opposite ends of the body 111 to complete the pump.

Body 111 has a cylindrical sleeve 117 surrounding chamber 112. A plurality of inwardly projected annular ribs or lands 118 are circumferentially spaced around sleeve 117. Ribs 118 terminate at their opposite ends in end stop members or projections 119 and 121. End stop members 119 and 121 cooperate with piston 113 to fix the end or terminal locations of piston 113 at the opposite ends of chamber 112. Piston 113 divides the chamber 112 into a first or left chamber 112A and a second or right chamber 112B.

Referring to FIG. 7, piston 113 has a core 122 carrying a ferromagnetic metal ring 123. Ring 123 is a cylindrical member and can be made of iron, cobalt-iron alloy, and like materials. A skin or outer layer 124 surrounds core 122 and ring 123. Skin 124 can be a pyrolite carbon material. Other types of skin or coating materials can be applied to the core and ring. Piston 113 has a generally cylindrical outer surface or wall 126 that engages the outer edges of ribs 118. Surface 126 is spaced from the inside surface of annular sleeve 117 by a plurality of spaces or arcuate passages 127 which allow the blood to flow around piston 113 as it moves in chamber 112. Piston 113 reciprocates between the opposite ends of chamber 112 and rotates about its longitudinal axis, thereby providing the piston with a minimum of wear as it slides on the outer edges of ribs 118. A limited amount of blood moving through spaces 127 between adjacent ribs 118 washes the outer surface of the piston 113 and wall 117 and also provides lubrication for piston 113.

End assembly 114 has a circular plate or housing 128 located in engagement with the left end of annular sleeve 117. Housing 128 has a central opening 129 in communication with chamber 112A. An inlet nipple 131 projects outwardly from plate 128 and has an inlet passage 133. A second or outlet nipple 132 projects outwardly from plate 128 and has an outlet passage 134. Passages 133 and 134 are in communication with the opening or vestibule chamber 129.

A one-way valve unit indicated generally at 136 is located in passage 133. Valve unit 136 allows the flow of blood into opening 129 and chamber 112A. When valve unit 136 is in its closed position, it restricts the reverse flow of blood through passage 133. Valve unit 136 comprises a circular disc 137 located in passage 133. Two pairs of pivots or pivot members 138 and 139 pivotally mount the disc on the nipple 131 for movement about offset from the center of the disc allowing the disc to pivot between its open and closed position, as shown in solid and broken lines.

A second one-way valve unit 137 is interposed in the passage 134 to control the flow of fluid out of the chamber 112A. When valve unit 141 is in the closed position, it restricts the reverse flow or inlet flow of fluid through passage 154 into the chamber 112A. Valve unit 141 comprises a circular disc 142 that is pivotally mounted on two pairs of pivot members 143 and 144. The pivot members 143 and 144 are operative to control the off center pivotal movement of the disc 142 between its open and closed positions while it retains the disc in its operative relationship with the inside walls of the nipple 132.

An end assembly 116 is identical with end assembly 114. Assembly 116 has a plate or housing 146 surrounding an opening or vestibule chamber 147. Opening 147 is in communication with the right end of chamber 112B. Housing 114 includes an inlet nipple 148 and an outlet nipple 149. Inlet nipple 148 has an inlet passage 151 accommodating a one-way valve unit indicated generally at 153. Outlet nipple 149 has an outlet passage 153 accommodating a one-way valve unit indicated generally at 158. Inlet and outlet passages 151 and 152 are in communication with the vestibule chamber 129.

One-way valve unit 153 includes a pivoting disc 154 that is mounted for off-center pivotal movement on pairs of pivot members 156 and 157. Valve unit 153 functions to allow the blood to flow into passage 151 into the opening 147 and chamber 112B and restrict reverse flow of blood through passage 151.

One-way valve unit 158 has a disc 159 that is pivoted off center on a pair of pivot members 161 and 162. Valve unit 158 allows blood to flow out of chamber 112B and restricts the reverse flow or inflow of blood into the chamber 112B. Other types of one-way valves, as ball valves and double leaflet valves, can be used to control the flow of blood through passages 133, 134, 151 and 152. Examples of suitable oneway valves are shown in U.S. Pat. No. 3,835,475.

A first winding or solenoid coil 163 is wound around the left half of sleeve 117. A second winding or solenoid coil 164 is wound around the right half of sleeve 117. An annular ring 106 is interposed between the adjacent ends of the solenoids 163 and 164. A pair of cover sleeves 167 and 168 surround the solenoids 163 and 164, respectively. Ring 166 has a pair of grooves 169 that accommodate the ends of the sleeves 167 and 168. Similar grooves are on the inside surfaces of plates 128 and 146, respectively, to accommodate the opposite or outer ends of the sleeves 167 and 168.

Referring to FIG. 5, an electrical control 174 is used to selectively energize solenoid coils 163 and 164. Control 174 is coupled to a power source 176, such as a battery or an outside source of power. Conductor lines 177 connect control 174 to solenoid 163. Conductor lines 178 connect the control 174 with solenoid 164. The control 174 is operable to control the cycling frequency of the solenoids 163 and 164 and the amount of current supplied to the solenoids.

In use, the solenoids 163 and 164, when energized, establish sequential reverse magnetic forces that reciprocate piston 113 in chamber 112. The energization of solenoid 163 will move the piston 113 to the left, thereby forcing the blood in chamber 112A through the outlet opening 134. One-way valve 136 will remain closed, whereby the blood opens the one-way valve 141.

When the solenoid 164 is energized, piston 113 moves to the right, thereby moving the blood in chamber 112B out through the passage 152. One-way valve 158 will open. The inlet one-way valve 153 will close. During the movement of piston 113 to the right blood will flow through passage 133 as the one-way valve 136 is open into chamber 112. The piston 113, being enlarged on the left side, fills in part of the chamber 112A so that a smaller quantity of blood is pumped from chamber 112A than is pumped from the larger chamber 112B. Piston 113 can be symmetrically balanced, such as the piston 113 shown in FIG. 3. This will provide for an equal amount of pumping of blood from each of the chambers on the opposite sides of piston 113.

Whiel there have been shown and described the preferred embodiments of the invention, it is understood that changes in the structure, size, valves, pistons, solenoids, and controls for the solenoids can be made by those skilled in the art without departing from the invention. The invention is defined in the following Claims.

The embodiments of the invention in which an exclusive property or privilege is claimed are defined as follows:

1. A pump for moving a fluid comprising: a body having first and second ends and a chamber open to said ends, said body having an inside wall surrounding the chamber, said wall having a plurality of longitudinal inwardly directed ribs, a first end member mounted on the first end of the body, a second end member mounted on the second end of the body, each of said end members having fluid inlet and fluid outlet passages, one-way inlet valve means in the inlet passages to control the flow of fluid into the opposite ends of the chamber, one-way outlet valve means in the outlet passages to control the flow of fluid out of the opposite ends of the chamber, a piston located in the chamber, said ribs being engageable with the piston to space the piston from the inside wall surrounding the chamber whereby a limited amount of fluid flows around the piston when the piston moves in the chamber, said piston being free to move in said chamber between the first and second end members, said piston including magnetic material, solenoid means for establishing sequential reverse magnetic force, and control means connected to the solenoid means to provide electric energy to energize the solenoid means whereby the sequential reverse magnetic force of the solenoid means acting on the magnetic material reciprocates the piston in the chamber, thereby moving fluid into and out of the opposite ends of the chamber through the inlet and outlet passages.

2. The pump of claim 1 wherein: the piston has a cylindrical outer surface located in a contiguous relationship with the ribs.

3. The pump of claim 1 including: stop members on opposite ends of the ribs to limit the reciprocating movement of the piston in the chamber.

4. The pump of claim 1 wherein: the piston has a core, a ring of magnetic material associated with the outer portion of the core, and an outer skin covering the core and ring.

5. The pump of claim 4 wherein: the outer skin is a pyrolite carbon material.

6. The pump of claim 1 wherein: the solenoid means extends the full length of the body, and a casing covers the solenoid means.

7. The pump of claim 1 wherein: each end member has a chamber in communication with the body chamber.

8. The pump of claim 1 wherein: each one-way inlet valve means and each one-way outlet valve means has a movable valving member.

9. The pump of claim 8 wherein: the movable valving member is a pivoting disc.

10. The pump of claim 1 wherein: each end member has a pair of tubular extensions having inlet and outlet passages leading to the chamber.

11. The pump of claim 1 wherein: the solenoid means includes a pair of solenoids surrounding the body.

12. The pump of claim 11 wherein: the pair of solenoids includes a first solenoid surrounding one end of the body and a second solenoid surrounding the opposite end of the body.

13. The pump of claim 1 wherein: the piston has a ring of magnetic material located adjacent one side of the piston.

14. A pump for moving a fluid comprising: a body having first and second ends and a chamber open to said ends, said body having a plurality of longitudinal ribs projected into the chamber, a first end member mounted on the first end of the body, a second end member mounted on the second end of the body, each of said end members having fluid inlet and fluid outlet passages, one-way inlet valve means in the inlet passage to control the flow of fluid into the opposite ends of the chamber, one-way outlet valve means in the outlet passages to control the flow of fluid out of the opposite ends of the chamber, a piston located in the chamber, said longitudinal ribs being engageable with the piston located in the chamber, said piston being free to move in said chamber between the first and second end members, said piston including magnetic material, solenoid means for establishing sequential reverse magnetic force, and control means connected to the solenoid means to provide electric energy to energize the solenoid means whereby the sequential reverse magnetic force of the solenoid means acting on the magnetic material reciprocates the piston in the chamber thereby moving fluid into and out of the opposite ends of the chamber through the inlet and outlet passages.

15. The pump of claim 4 including: stop members associated with opposite ends of the ribs to limit the reciprocating movement of the piston in the chamber.

16. The pump of claim 14 wherein: the piston has a core, a ring of magnetic material associated with the outer portion of the core, and an outer skin covering the core and ring.

17. The pump of claim 16 wherein: the outer skin is a pyrolite carbon material.

18. The pump of claim 14 wherein: each one-way inlet valve means and each one-way outlet valve means has a pivoting disc valving member.

19. The pump of claim 14 wherein: the solenoid means includes a pair of solenoids surrounding the body.

20. A pump for moving a fluid comprising: means having a chamber and inlet and outlet passages in communication with opposite ends of the chamber, one-way inlet valve means operable to allow fluid to flow through the inlet passage into the opposite ends of the chamber and restrict flow of fluid out of the chamber, one-way outlet valve means operable to allow fluid to flow through the outlet passage out of the chamber and restrict flow of fluid into the chamber, a movable piston means located in the chamber, said piston means having a core, a ring of magnetic material associated with the core, an outer skin covering the core and ring, solenoid means associated with said means having a chamber for establishing sequential reverse magnetic force, and control means connected to the solenoid means whereby the sequential reverse magnetic force acting on the magnetic material of the piston means moves the piston means in a manner to move fluid into and out of the opposite ends of the chamber.

21. The pump of claim 20 wherein: the means having a chamber includes a body having a cylindrical chamber.

22. The pump of claim 20 wherein: the means having a chamber and an inlet and outlet passage including a body having a cylindrical chamber, first end means mounted on one end of the body, and second end means mounted on the opposite end of the body, each of said end means having an inlet passage and an outlet passage in communication with the associated end of the chamber.

23. The pump of claim 20 wherein: each one-way inlet valve means and each one-way outlet valve means has a movable valving member.

24. The pump of claim 23 wherein: the movable valving member is a pivoting disc.

25. The pump of claim 20 wherein: the outer skin is a pyrolite carbon material.

26. The pump of claim 20 wherein: the outer skin is a wear-resistant biologically inert material.

27. The pump of claim 20 wherein: the movable piston has a disc shape.

28. The pump of claim 20 wherein: the means having a chamber includes an inside wall surrounding the chamber, said wall having a plurality of longitudinally extended ribs, said ribs extended into the chamber and engageable with the piston means to space the piston means from said wall whereby a limited amount of fluid flows around the piston means when the piston means moves in the chamber.

29. The pump of claim 28 including: stop members on opposite ends of the ribs to limit the reciprocating movement of the piston means in the chamber.

30. The pump of claim 20 wherein: the solenoid means extends substantially the full length of the means having a chamber and include a casing for covering the solenoid means.

31. The pump of claim 20 wherein: the solenoid means include a pair of solenoids surrounding the means having a chamber.

32. The pump of claim 31 wherein: said pair of solenoids includes a first solenoid surrounding one end section of the means having a chamber and a second solenoid surrounding the opposite end section of the means having a chamber.

33. The pump of claim 20 wherein: the ring of magnetic material is located adjacent one side of the piston means.

34. A pump for moving fluid comprising: a body having a first end and second end and chamber opened to said ends, a first end member mounted on the first end of the body, a second end member mounted on the second end of the body, each of said end members having fluid inlet and fluid outlet passages, one-way inlet valve means in the inlet passage to control the flow of fluid into the opposite ends of the chamber, one-way outlet valve means in the outlet passages to control the flow of fluid out of the opposite ends of the chamber, a piston located in the chamber, said piston having a core, a ring of magnetic material associated with the outer portion of the core, and an outer skin covering the core and the ring, said piston being free to move in said chamber between the first and second end members, said piston including magnetic material, solenoid means for establishing sequential reverse magnetic force, and control means connected to the solenoid means to provide electric energy to energize the solenoid means whereby the sequential reverse magnetic force of the solenoid means acting on the magnetic material reciprocates the piston in the chamber thereby moving fluid into and out of the opposite ends of the chamber through the inlet and outlet passages.

35. The pump of claim 34 wherein: the outer skin is a pyrolite carbon material.

36. The pump of claim 34 wherein: the body has a plurality of longitudinal ribs projected into the chamber, said ribs being engagable with the outer skin of the piston.

37. The pump of claim 36 including: stop members on opposite ends of the ribs to limit reciprocating movement of the piston in the chamber.

38. The pump of claim 34 wherein: the ring of magnetic material is located adjacent one side of the piston.

39. The pump of claim 34 wherein: each one-way inlet valve means and each one-way outlet valve means has a pivoting disc valving member.

40. The pump of claim 34 wherein: the solenoid means includes a pair of solenoids surrounding the body.

41. A pump for moving a fluid comprising: a body having first and second ends and a chamber open to said ends, said body having an inside wall surrounding the chamber, a first end member mounted on the first end of the body, a second end member mounted on the second end of the body, each of said end members having fluid inlet and fluid outlet passages, one-way inlet valve means in the inlet passages to control the flow of fluid into the opposite ends of the chamber, one-way outlet valve means in the outlet passages to control the flow of fluid out of the opposite ends of the chamber, a piston located in the chamber, said piston having a ring of magnetic material located adjacent one side of the piston, said piston being free to move in said chamber between the first and second end members, solenoid means for establishing sequential reverse magnetic force, and control means connected to the solenoid means to provide electric energy to energize the solenoid means whereby the sequential reverse magnetic force of the solenoid means acting on the magnetic material reciprocates the piston in the chamber, thereby moving fluid into and out of the opposite ends of the chamber through the inlet and outlet passages.

42. The pump of claim 41 including: an outer skin covering the ring of magnetic material.

43. The pump of claim 42 wherein: the outer skin is a pyrolite carbon material.

44. The pump of claim 41 including: ribs on said inside wall, and stop members on opposite ends of the ribs to limit reciprocating movement of the piston in the chamber.

45. The pump of claim 41 wherein: the solenoid means includes a pair of solenoids surrounding the body.

46. A pump for moving a fluid comprising: means having a chamber and inlet and outlet passages in communication with opposite ends of the chamber, said means including an inside wall surrounding the chamber, said wall having a plurality of longitudinally extended ribs, said ribs extended into the chamber, one-way inlet valve means operable to allow fluid to flow through the inlet passage into the opposite ends of the chamber and restrict the flow of fluid out of the chamber, one-way outlet valve means operable to allow fluid to flow through the outlet passage out of the chamber and restrict the flow of fluid into the chamber, a movable piston means located in the chamber, said piston means being engageable with the ribs to space the piston means from the wall whereby a limited amount of fluid flows around the piston means when the piston means moves in the chamber, said piston means having magnetic material, solenoid means associated with said means having a chamber for establishing sequential reverse magnetic force, and control means connected to the solenoid means operable to provide electric energy to energize the solenoid means whereby the sequential reverse magnetic force acting on the magnetic material of the piston means moves the piston means in a manner to move the fluid into and out of the opposite ends of the chamber.

47. The pump of claim 46 wherein: the means having a chamber and an inlet and outlet passage including a body having a cylindrical chamber, first end means mounted on one end of the body, and second end means mounted on the opposite end of the body, each of said end means having an inlet passage and an outlet passage in communication with the associated end of the chamber.

48. The pump of claim 46 wherein: each one-way inlet valve means and each one-way outlet valve means has a movable valving member.

49. The pump of claim 48 wherein: the movable valving member is a pivoting disc.

50. The pump of claim 48 wherein: the movable piston means has a core, a ring of magnetic material associated with the core, and an outer skin covering the core and ring.

51. The pump of claim 50 wherein: the outer skin is a wearresistant biologically inert material.

52. The pump of claim 46 including: stop members on opposite ends of the ribs to limit the reciprocating movement of the valving means in the chamber.

53. The pump of claim 46 wherein: the solenoid means include a pair of solenoids surrounding the means having a chamber.

54. The pump of claim 53 wherein: said pair of solenoids includes a first solenoid surrounding one end section of the means having a chamber and a second solenoid surrounding the opposite end section of the means having a chamber.

55. The pump of claim 46 wherein: the magnetic material is a ring of magnetic material located adjacent one side of the piston means.

* * * * *

UNITED STATES PATENT AND TRADEMARK OFFICE
CERTIFICATE OF CORRECTION

PATENT NO. : 4,221,548
DATED : September 9, 1980
INVENTOR(S) : Frank W. Child

It is certified that error appears in the above-identified patent and that said Letters Patent are hereby corrected as shown below:

Column 2, line 39, "piston 15" should be -- piston 13 --.

Column 5, line 54, "ring 106" should be -- ring 166 --.

Column 6, line 25, "Whiel" should be -- While --.

Column 8, line 15, after "to the solenoid means" insert -- operable to provide electric energy to energize solenoid means --.

Signed and Sealed this

Thirtieth Day of December 1980

[SEAL]

Attest:

SIDNEY A. DIAMOND

Attesting Officer

Commissioner of Patents and Trademarks